US00PP10144P

United States Patent [19]

van Andel

[11] Patent Number: Plant 10,144

[45] Date of Patent: Dec. 9, 1997

[54] ALSTROEMERIA PLANT VARIETY NAMED 'STADELIL'

[75] Inventor: Jacob van Andel, Aalsmeer, Netherlands

[73] Assignee: Van Staaveren b.v., Netherlands

[21] Appl. No.: 629,869

[22] Filed: Apr. 10, 1996

[51] Int. Cl.[6] ..... A01H 5/00

[52] U.S. Cl. ..... Plt./87.1

[58] Field of Search ..... Plt./87.1

*Primary Examiner*—James R. Feyrer

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria originated as a seedling by crossing as seed parent an unreleased, unpatented seedling identified as 86R776-1 and as pollen parent an unreleased, unpatented seedling identified as 87G737-2 from among my collection of Alstroemeria seedlings maintained under controlled conditions in a greenhouse at Van Staaveren B.V., Aalsmeer, The Netherlands, for developmental purposes. The varietal denomination of the new variety is 'Stadelil'.

The first act of asexual reproduction of 'Stadelil' was in Aalsmeer, The Netherlands, by propagation by dividing rootstocks. Asexual reproduction through successive generations has demonstrated that the combination of characteristics as herein disclosed for 'Stadelil' are firmly fixed and retained through successive generations of asexual reproduction.

'Stadelil' has not been observed under all possible environmental conditions. Phenotypic expression may vary with variations in environment such as temperature, light intensity, day length and growing and cultural conditions.

SUMMARY OF THE INVENTION

Flowers of the new variety of Alstroemeria, 'Stadelil' are characterized by flowers of unusual coloration, as described herein.

The new variety blooms profusely with good annual production, including production of flower stems in winter under greenhouse conditions in The Netherlands, which is a desirable characteristic in a cut flower variety. 'Stadelil' grows productively under greenhouse conditions and is also reproducible both by division of rhizomes and by tissue culture.

DESCRIPTION OF ILLUSTRATIONS

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:
- *Family.*—Amaryllidaceae.
- *Genus.*—Alstroemeria sp.
- *Commercial.*—Alstroemeria hybrid.

Origin: Seedling.

Plant

Form: Bush.
Shape: Upright.
Height: About 130 to 180 cm.
Internode length: About 1 to 4 cm.
Growth rate: Medium.
Main stem or cane length: About 160 cm.
Growth: Vigorous.
Strength: Strong.
Foliage:
- *Quantity.*—Abundant.
- *Number of leaves.*—About 25 to 30 per stem.
- *Size of leaf.*—Length: About 14 to 18 cm. Width: About 3 to 4 cm.
- *Shape of leaf.*—Elliptical.
- *Margin type.*—Straight.
- *Texture.*—Glossy.
- *Color.*—Under side: Near 137A. Underside: Near 137C.
- *Rhizomes.*—Yes. Color: Near 155D. Size: About 10 to 30 cm.

Inflorescence—Flower

Blooming habit: Recurrent.
Blooms: Profusely.
- *Spring.*—Yes.
- *Fall.*—Yes.
- *Has tendency to give few blooms in fall.*—No.

Size: Very large.
- *Diameter.*—About 6 cm.
- *Depth.*—About 5 cm.

Borne: Progressively along simple racemes.
Shape or form:
- *When bloom first opens.*—Funnelform.
- *When bloom matures.*—Funnelform.

Production: Good annual production, including production of flower stems in winter under greenhouse conditions in The Netherlands.
Petalage:
- *Number of petals.*—6.
- *Arrangement.*—2 concentric circles of 3 petals.
- *Form.*—Obovate.

*Margin type.*—Minutely crimped.

*Apex.*—Outer petals broadly cuspidate; inner petals narrowly cuspidate.

*How long do petals stay on stem?*—About 3 weeks.

*Texture.*—Soft.

*Appearance.*—Velvety.

*Color (summer/fall).*—Outer petal/floret: Body near 68A; base near 68A; reverse side near 68A; no stripes. Inside lateral petal: Apical portions are red-purple near 68A which changes abruptly, to bright yellow, near 12A in a band across the central portion of these petals. The bright yellow, bleeds gradually into a light shade of red-purple, near 43D toward the claw of each inside lateral petal. The color patterns and shadings of the reverse sides follow those of the top surface. Each inside lateral petal contains about 23 to 25 elongated stripes, near 71A in coloration, mostly isolate within the bright yellow 12A to 43D and basal portions of the petals. Inside median petal: Body near 68A to 12C; base near 68D; reverse side near 68A; 8 to 12 stripes, near 71A; bright yellow coloration is scant and may not be continuous across the central portion of the inside median petal.

Peduncle or flower stem:

*Length.*—About 6 to 8 cm.

*Color.*—Near 137B to 137C.

*Strength.*—Strong.

*Upright.*—Yes.

Discoloration after full bloom? Slightly.

Is bloom affected by wet or hot weather? No.

Persistence (does flower hang on and dry?): No.

Disease resistance: Unknown.

Fragrance: None.

Lasting quality:

*On plant.*—About 3 weeks.

*As cut flower.*—About 14 days.

Bud

Size:

*Diameter.*—About 1 to 2 cm.

*Depth of length.*—About 2 to 3 cm.

Form or shape: Pear-shaped.

*Long.*—2 to 3 cm.

*Pointed.*—No.

Rate of opening: Fast.

Color of petals/florets:

*When petals begin to unfurl.*—Near 67A.

Reproductive Organs

Stamen:

*Number.*—6.

*Arrangement.*—Around the style.

Anthers:

*Size.*—About 3 to 4 mm.

*Color.*—Near 4C.

Filaments:

*Length.*—About 2 to 3 cm.

*Color.*—Near 65D.

Pollen:

*Color.*—No pollen formed.

Pistils:

*Number.*—1.

Styles:

*Length.*—About 4 to 5 cm.

*Color.*—Near 64C to 64D.

Stigmas:

*Color.*—Near 64C to 64D.

Fruit

Fertile: Yes.

Shape: Round.

Color at maturity: Near 163A.

I claim:

1. A new variety of Alstroemeria plant, substantially as herein shown and described.

* * * * *

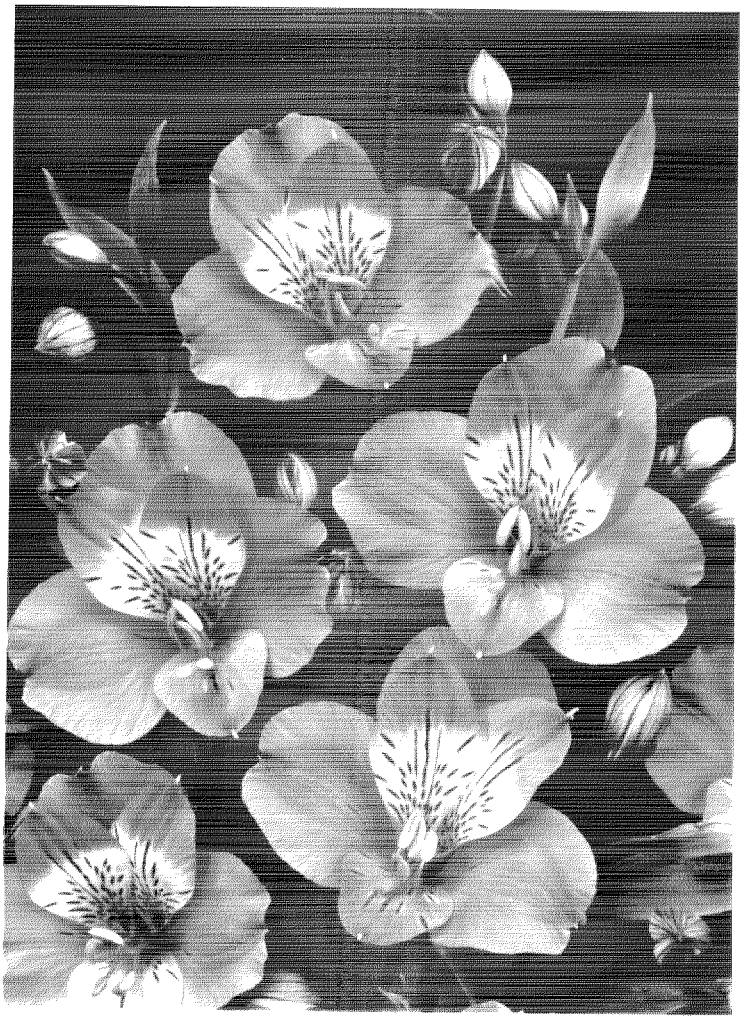

UNITED STATES PATENT AND TRADEMARK OFFICE

CERTIFICATE OF CORRECTION

PATENT NO. : Plant 10,144

DATED : December 9, 1997

INVENTOR(S) : Jacob van Andel

It is certified that error appears in the above-indentified patent and that said Letters Patent is hereby corrected as shown below:

Column 2, line 26, replace "Under" with -- Upper --.

Signed and Sealed this

Eighth Day of September, 1998

*Attest:*

*Attesting Officer*

BRUCE LEHMAN

*Commissioner of Patents and Trademarks*